(12) United States Patent
St. George

(10) Patent No.: US 11,730,345 B2
(45) Date of Patent: Aug. 22, 2023

(54) SHEATH FOR AN ENDOSCOPE

(71) Applicant: Gyrus ACMI, Inc., Southborough, MA (US)

(72) Inventor: Lawrence J. St. George, Sudbury, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 733 days.

(21) Appl. No.: 15/738,351

(22) PCT Filed: Jan. 12, 2016

(86) PCT No.: PCT/US2016/013026
§ 371 (c)(1),
(2) Date: Dec. 20, 2017

(87) PCT Pub. No.: WO2017/003514
PCT Pub. Date: Jan. 5, 2017

(65) Prior Publication Data
US 2018/0184885 A1 Jul. 5, 2018

Related U.S. Application Data

(60) Provisional application No. 62/186,090, filed on Jun. 29, 2015.

(51) Int. Cl.
A61B 1/00 (2006.01)
A61B 1/015 (2006.01)
(Continued)

(52) U.S. Cl.
CPC ........ *A61B 1/00135* (2013.01); *A61B 1/0014* (2013.01); *A61B 1/00073* (2013.01);
(Continued)

(58) Field of Classification Search
CPC ............ A61B 1/00135; A61B 1/00142; A61B 1/00082; A61B 1/00094; A61B 1/0014;
(Continued)

(56) References Cited

U.S. PATENT DOCUMENTS 4,141,364 A 2/1979 Schultze
5,025,778 A * 6/1991 Silverstein ......... A61B 1/00078
600/104
(Continued)

FOREIGN PATENT DOCUMENTS

CA 2143639 C 7/2004
CN 108235680 A 7/2018
(Continued)

OTHER PUBLICATIONS

"European Application Serial No. 16704081.5, Communication Pursuant to Article 94(3) EPC dated Jul. 24, 2020", 5 pgs.
(Continued)

*Primary Examiner* — Ryan N Henderson
*Assistant Examiner* — Pamela F Wu
(74) *Attorney, Agent, or Firm* — Schwegman Lundberg & Woessner, P.A.

(57) ABSTRACT

A sheath includes a sheath body, an inflow port at a proximal end of the sheath body, an outflow port at the proximal end of the sheath body, and a plurality of radially expandable flexible members which extend along a length of the sheath body. The plurality of radially expandable flexible members are attached to the sheath body at a plurality of anchor points along the length of the sheath body. The plurality of radially expandable flexible members expand during active fluid inflow. The radially expandable flexible members are spaced apart along the sheath body to define one or more isolated spaces that extend between adjacent radially expandable
(Continued)

flexible members when the radially expandable flexible members are inflated within a body passage.

8 Claims, 6 Drawing Sheets

(51) Int. Cl.
| | |
|---|---|
| *A61B 1/307* | (2006.01) |
| *A61M 25/06* | (2006.01) |
| *A61B 17/22* | (2006.01) |
| *A61M 1/00* | (2006.01) |
| *A61M 3/02* | (2006.01) |
| *A61M 25/00* | (2006.01) |
| *A61B 17/00* | (2006.01) |

(52) U.S. Cl.
CPC ...... *A61B 1/00082* (2013.01); *A61B 1/00094* (2013.01); *A61B 1/015* (2013.01); *A61B 1/307* (2013.01); *A61B 17/22* (2013.01); *A61M 1/77* (2021.05); *A61M 3/0283* (2013.01); *A61M 25/0662* (2013.01); *A61B 2017/00022* (2013.01); *A61B 2017/00084* (2013.01); *A61B 2017/22051* (2013.01); *A61B 2017/22069* (2013.01); *A61B 2217/007* (2013.01); *A61M 1/772* (2021.05); *A61M 3/0279* (2013.01); *A61M 2025/004* (2013.01); *A61M 2025/0024* (2013.01); *A61M 2025/0681* (2013.01); *A61M 2205/3334* (2013.01); *A61M 2205/3368* (2013.01)

(58) Field of Classification Search
CPC ......... A61B 1/015; A61B 1/307; A61B 1/012; A61B 1/12; A61B 1/126–128; A61B 1/00131; A61B 1/00073; A61B 1/00075; A61B 1/00091; A61B 1/00144; A61M 3/0283; A61M 3/0291; A61M 3/0295; A61M 25/00; A61M 25/0021; A61M 25/0023; A61M 2025/0001–0004; A61M 2025/0024–0025; A61M 25/0026–0029; A61M 25/003; A61M 2025/0034–0037; A61M 2025/0681; A61M 25/0662
USPC .......................................... 600/115, 121, 123
See application file for complete search history.

(56) References Cited

U.S. PATENT DOCUMENTS

| | | | | |
|---|---|---|---|---|
| 5,217,001 A | * | 6/1993 | Nakao ................ | A61B 1/00135 24/DIG. 50 |
| 5,503,616 A | * | 4/1996 | Jones ................. | A61B 1/00135 600/121 |
| 6,458,076 B1 | | 10/2002 | Pruitt | |
| 6,554,794 B1 | | 4/2003 | Mueller | |
| 8,360,968 B2 | | 1/2013 | Hadani | |
| 8,597,261 B2 | | 12/2013 | Knapp | |
| 8,652,029 B2 | * | 2/2014 | Hotto ................. | A61B 1/00082 600/121 |
| 2002/0045852 A1 | * | 4/2002 | Saab ....................... | A61F 7/123 604/96.01 |
| 2002/0143237 A1 | * | 10/2002 | Oneda ................ | A61B 1/00156 600/116 |
| 2005/0159728 A1 | | 7/2005 | Armour et al. | |
| 2008/0172033 A1 | | 7/2008 | Keith et al. | |
| 2009/0259172 A1 | | 10/2009 | Yamaoka et al. | |
| 2010/0256447 A1 | * | 10/2010 | Dubi ....................... | A61B 1/31 600/115 |
| 2011/0092766 A1 | | 4/2011 | Bapaye et al. | |
| 2011/0313242 A1 | | 12/2011 | Surti | |
| 2015/0018620 A1 | | 1/2015 | Oneda et al. | |
| 2015/0196735 A1 | | 7/2015 | Olig | |

FOREIGN PATENT DOCUMENTS

| | | | |
|---|---|---|---|
| EP | 3313261 | A1 | 5/2018 |
| EP | 3313261 | B1 | 6/2021 |
| ES | 2881748 | T3 | 11/2021 |
| IN | 201737045970 | A | 2/2018 |
| IN | 202138049383 | A | 3/2022 |
| JP | 2008504067 | A | 2/2008 |
| JP | 2008538709 | A | 11/2008 |
| JP | 2011512942 | A | 4/2011 |
| JP | 2013121385 | A | 6/2013 |
| JP | 2016525900 | A | 9/2016 |
| JP | 2017155817 | A | 9/2017 |
| JP | 2018520760 | A | 8/2018 |
| JP | 8588994 | B2 | 9/2019 |
| JP | 2020006212 | A | 1/2020 |
| JP | 6874077 | B2 | 4/2021 |
| WO | WO-2017003514 | A1 | 1/2017 |

OTHER PUBLICATIONS

"Japanese Application Serial No. 2019-166730, Notification of Reasons for Refusal dated Sep. 8, 2020", 9 pgs.
"Chinese Application Serial No. 201680038132.0, Office Action dated Mar. 31, 2020", w/English Translation, 14 pgs.
"Chinese Application Serial No. 201680038132.0, Office Action dated Aug. 5, 2019", w/English Translation, 17 pgs.
"Chinese Application Serial No. 201680038132.0, Response filed Jun. 12, 2020 to Office Action dated Mar. 31, 2020", w/ English Claims, 9 pgs.
"Chinese Application Serial No. 201680038132.0, Response filed Nov. 25, 2019 to Office Action dated Aug. 5, 2019", with English translation of claims, 10 pgs.
"European Application Serial No. 16704081.5, Communication Pursuant to Article 94(3) EPC dated Feb. 6, 2019", 6 pgs.
"European Application Serial No. 1604081.5, Response filed Jul. 31, 2018 to Communication Pursuant to Rules 161(1) and 162 EPC dated Feb. 6, 2018", 20 pgs.
"European Application Serial No. 16704081.5, Response filed Aug. 7, 2019 to Communication Pursuant to Article 94(3) EPC dated Feb. 6, 2019", 16 pgs.
"International Application Serial No. PCT/US2016/013026, International Preliminary Report on Patentability dated Jan. 11, 2018", 9 pgs.
"International Application Serial No. PCT/US2016/013026, International Search Report dated Apr. 6, 2016", 4 pgs.
"International Application Serial No. PCT/US2016/013026, Written Opinion dated Apr. 6, 2016", 6 pgs.
"Japanese Application Serial No. 2017-565817, Office Action dated Dec. 6, 2018", w/ English translation, 10 pgs.
"Japanese Application Serial No. 2017-565817, Response filed Jun. 6, 2019 to Office Action dated Dec. 6, 2018", w/ English translation, 6 pgs.
"Chinese Application Serial No. 201680038132.0, Office Action dated Nov. 16, 2020", w/English translation, 13 pgs.
"European Application Serial No. 16704081.5, Response filed Nov. 26, 2020 to Communication Pursuant to Article 94(3) EPC dated Jul. 24, 2020", 12 pgs.
"European Application Serial No. 21172251.7, Extended European Search Report dated Jul. 29, 2021", 7 pgs.
"Chinese Application Serial No. 201680038132.0, Office Action dated Jun. 2, 2021", w/English Translation, 13 pgs.
"Chinese Application Serial No. 201680038132.0, Response filed Jan. 27, 2021 to Office Action dated Nov. 16, 2020", w/English Claims, 54 pgs.
"Indian Application Serial No. 201737045970, First Examination Report dated May 2, 2021", 7 pgs.
"Japanese Application Serial No. 2019-166730, Response filed Feb. 4, 2021 to Notification of Reasons for Refusal dated Sep. 8, 2020", w/o Translation, 5 pgs.
"European Application Serial No. 21172251.7, Response filed Mar. 14, 2022 to Extended European Search Report dated Jul. 29, 2021", 16 pgs.

(56) References Cited

OTHER PUBLICATIONS

"Indian Application Serial No. 201737045970, Response filed Oct. 27, 2021 to First Examination Report dated May 2, 2021", w/english claims, 200 pgs.

"Indian Application Serial No. 202138049383, First Examination Report Received dated Jan. 5, 2023", 6 pgs.

* cited by examiner

SHEATH FOR AN ENDOSCOPE

RELATED APPLICATION

This application claims the benefit of U.S. Provisional Patent Application No. 62/186,090, filed on Jun. 29, 2015, the entire contents of which are incorporated herein by reference.

FIELD

The present disclosure relates to medical device. More specifically, the present disclosure relates to a sheath that is capable of receiving an insertion tube of an endoscope.

BACKGROUND

The statements in this section merely provide background information related to the present disclosure and may or may not constitute prior art.

During ureteroscopy procedures, baskets are often employed to capture and retrieve stone fragments from a patient's anatomy. Some stone fragments, however, may be left in the kidney because of the difficulty in capturing small fragments employing conventional stone baskets. The fragments that are not removed can act as nucleation sites for future stone formation. Typical corrective actions include follow-up monitoring for future stone formation and additional ureteroscopic procedures to remove the remaining stone fragments. Percutaneous nephrolithotomy (PCNL) may also be employed since PCNL often includes suction for removing stone fragments and dust.

Further, perforation or avulsion of the ureter is a possible complication during ureteroscopy, which may result in the loss and removal of the associated renal unit. The force required to avulse or perforate a human ureter is not very large. For example, a study in the "Journal of Urology, vol. 70(3), p. 592," states the force required to perforate a human ureter with a needle is $1.05 \pm 0.29$ $Ib_m$ or $0.79 \pm 0.25$ $Ib_m$ with a guidewire.

Among the literature that can pertain to this technology include the following patent documents and published patent applications: U.S. Pat. Nos. 6,458,076, 6,554,794, 8,360,968, 8,597,261, US 2005/0159728, US 2011/0313242, and US 2015/0018620, the entire contents of which are incorporated herein by reference for all purposes.

Accordingly, there is a need for a device that can be employed with an ureteroscopy procedure that removes small stone fragments and reduces the chances of ureter perforation or avulsion during the procedure.

SUMMARY

The present invention provides a sheath capable of receiving an insertion tube of an endoscope and a method of using such a sheath.

In one aspect, the sheath includes a sheath body, an inflow port at a proximal end of the sheath body, an outflow port at the proximal end of the sheath body, and a plurality of radially expandable flexible members which extend along a length of the sheath body. The plurality of radially expandable flexible members may be attached to the sheath body at a plurality of anchor points along the length of the sheath body. The plurality of radially expandable flexible members may expand during active fluid inflow. The radially expandable flexible members may be spaced apart along the sheath body to define one or more isolated spaces that extend between adjacent radially expandable flexible members when the radially expandable flexible members are inflated within a body passage.

The sheath may be further characterized by one or any combination of the features described herein, such as, for example: the sheath further includes a plurality of rigid channels which extend along the length of the sheath body; the channels of the plurality of rigid channels are attached to the sheath body at a plurality of anchor points; the channels of the plurality of rigid channels are attached to the plurality of expandable flexible members at a plurality of anchor points; the channels of the plurality of rigid channels are spaced apart to define one or more isolated spaces with the channels that extend along the length of the sheath body; fluid flows from a distal end of the sheath body though the isolated spaces to the outflow port during active fluid outflow; active fluid outflow removes debris from a body region; the active fluid inflow provides irrigation fluid to a body region; the sheath further includes a plurality of ribs which extend along the length of the sheath body; the ribs of the plurality of ribs are spaced apart to define one or more isolated spaces between adjacent ribs that extend along the length of the sheath body; fluid flows from a distal end of the sheath body though the isolated spaces to the outflow port during active fluid outflow; the sheath further includes one or more sensors located at a distal end of the sheath body; the one or more sensors measures at least one of pressure, temperature, and fluid flow rate; and the sheath includes a directional guide at a distal end of the sheath body to direct irrigation fluid during the active fluid inflow.

In another aspect, the present disclosure provides a method of irrigating a body region including one or more of the following steps: sliding a sheath body over an insertion tube of an endoscope; and pumping fluid into an inflow port at a proximal end of the sheath body to expand a plurality of radially expandable flexible members which extend along a length of the sheath body during active fluid inflow.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. Moreover, in the figures, like reference numerals designate corresponding parts throughout the views. In the drawings.

DETAILED DESCRIPTION

Figure 1A:
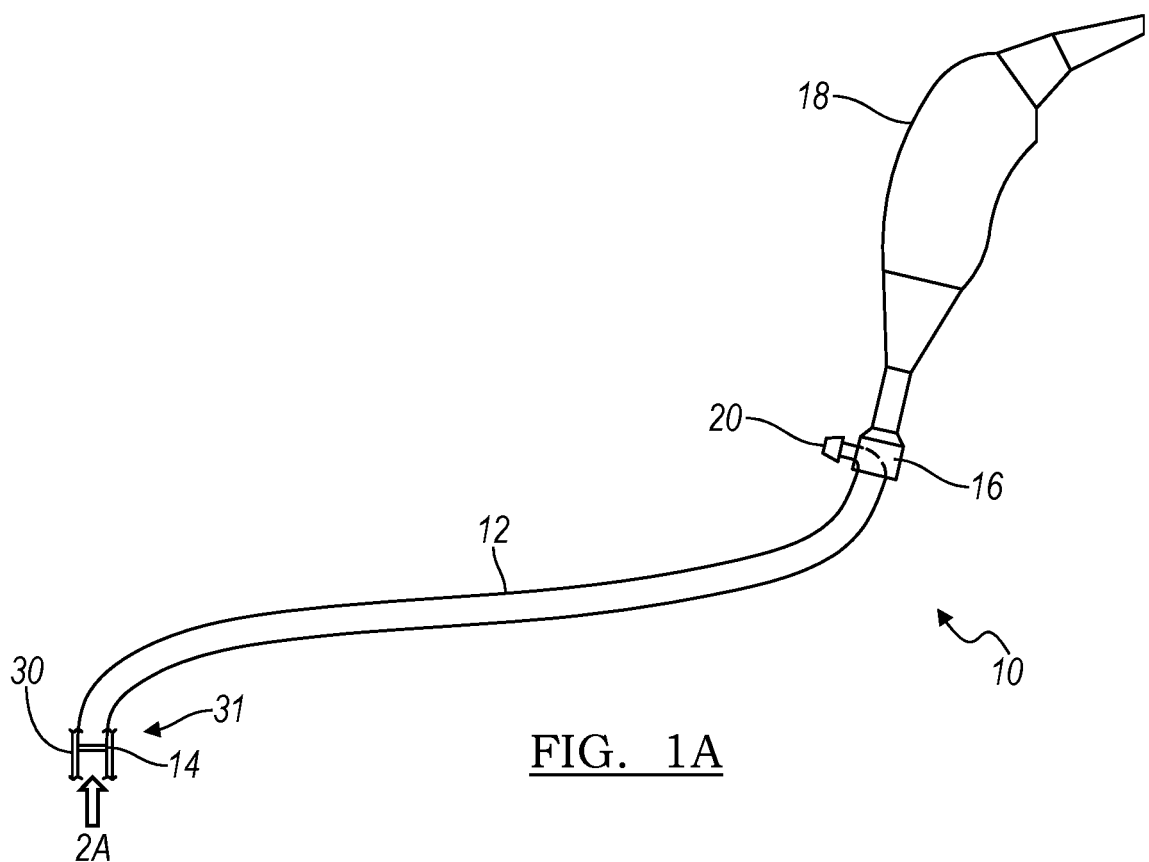
FIGS. 1A and 1B are schematic views of a sheath for an endoscope in accordance with the principles of the present invention.
Figure 1B:
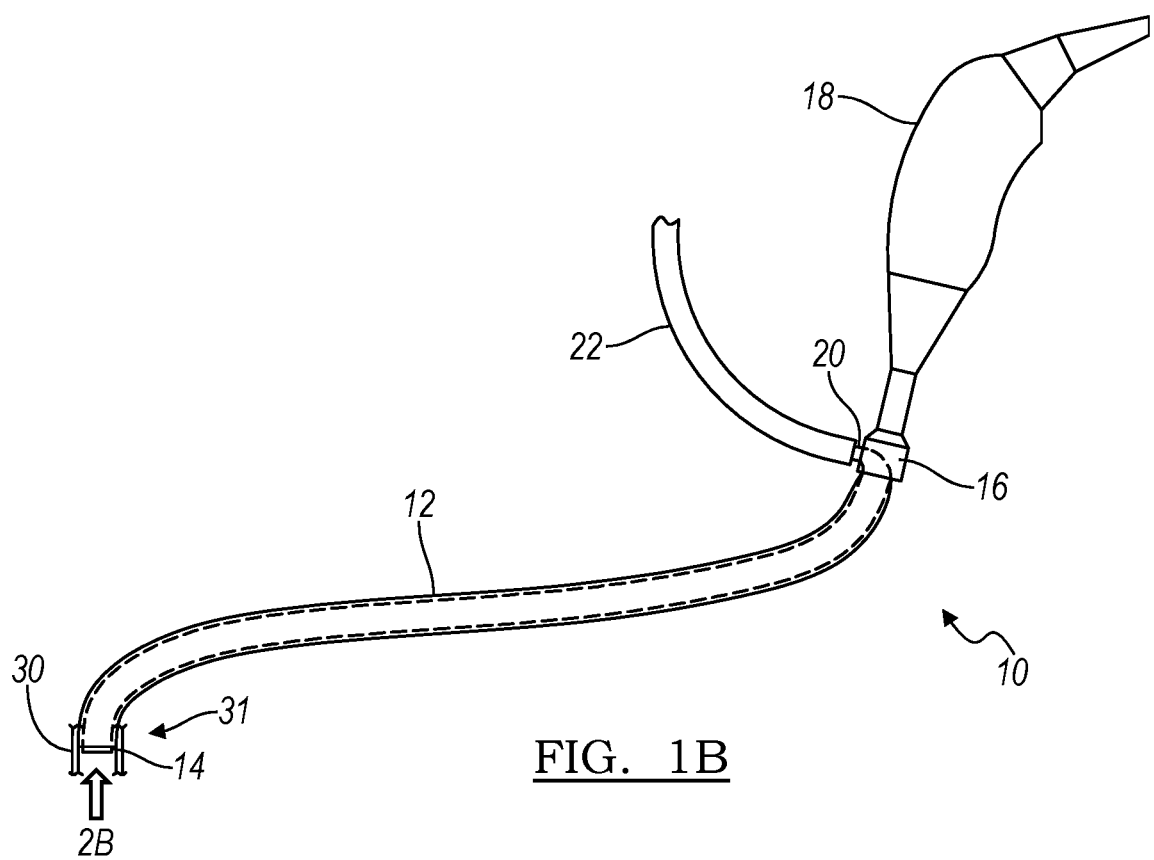

The following description is merely exemplary in nature and is not intended to limit the present disclosure, application, or uses.

Referring now to the drawings, a sheath 12 receiving an insertion tube 14 of an endoscope 10 in accordance with the principles of the present invention is illustrated in FIGS. 1A, 1B, 2A and 2B. The endoscope 10 further includes a handle portion 18 and a connector 16 that connects the handle portion 18 with the sheath 12 and insertion tube 14. The handle portion 18 may include components for operating the endoscope 10, such as, for optical components for imaging, fluid flow components for irrigation and control components for movement of the insertion tube 14 and sheath 12.

The connector 16 includes an inlet 20 that connects with a tube 22. The tube 22 provides fluid that flows through the inlet 20 into the sheath 12. In typical use, the insertion tube 14 and sheath 12 are inserted into a body passage such as a ureter 30.

Figure 2A:
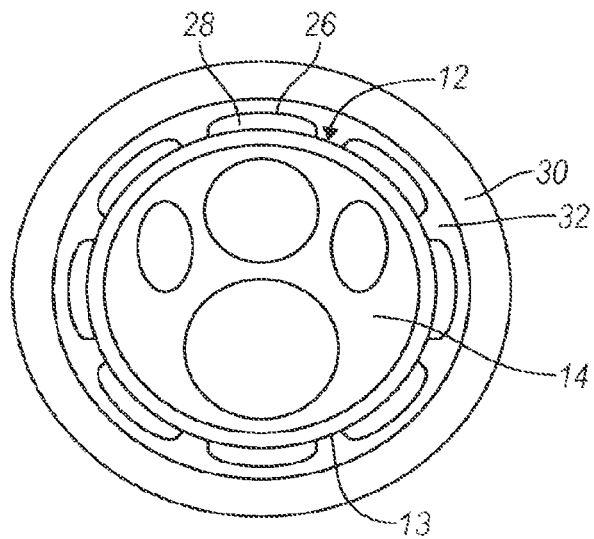
FIG. 2A is a view along 2A of FIG. 1A.
Figure 2B:
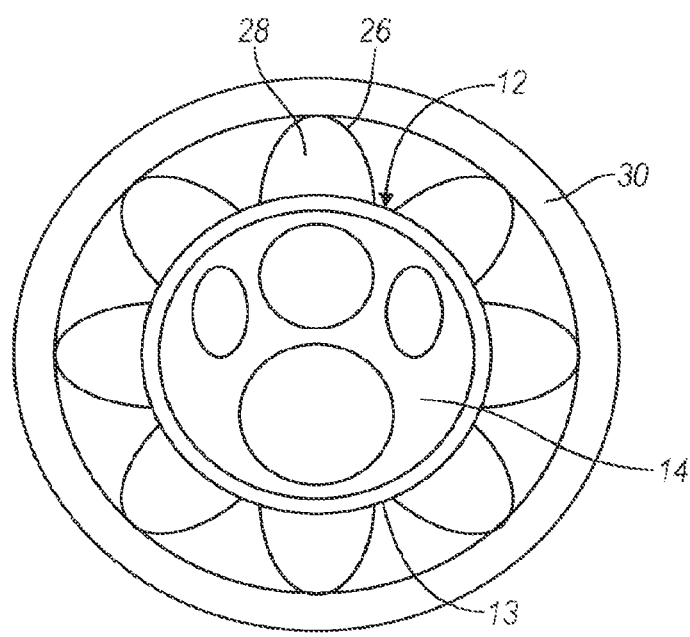
FIG. 2B is a view along 2B of FIG. 1B.

In a particular arrangement, the sheath 12 includes a plurality of radially expandable flexible members 26 which extend along the length of a sheath body 13. As shown in FIG. 2B, each of the plurality of radially expandable flexible members 26 has a generally petal shape when expanded. The plurality of radially expandable flexible members 26 are attached to the sheath body 13 at a plurality of anchor points along the length of the sheath body. The plurality of radially expandable flexible members 26 expand during active fluid inflow from the inlet 20 to a distal end 31 of the sheath 12. The radially expandable flexible members 26 are spaced apart along the sheath body 13 to define one or more isolated spaces 28 that extend between adjacent radially expandable flexible members 26 when the radially expandable flexible members are inflated within the ureter 30.

A region 32 including a plurality of outflow channels extends along the length of the sheath body 13. The region 32 may remove debris from a body region during active fluid outflow.

When the endoscope 10 is employed for a medical procedure, an operator of the endoscope 10, such as a physician, inserts the insertion tube 14 and the sheath 12 through a body passage such as the ureter 30 so that the distal end 31 of the sheath 12 is positioned at an anatomical region of interest. The anatomical region of interest may contain stone fragments that are removed during the medical procedure. The physician may use the optical components associated with the endoscope 10 to provide guidance of the insertion tube 14 through the ureter and to image the anatomical region of interest. The physician may also employ the control components associated with the endoscope 10 to maneuver the insertion tube 14. The stone fragments may be fragments produced by a prior procedure, or the stone fragments may be produced during the use of the endoscope 10.

As fluid is supplied through the tube 22, the pressure of the fluid expands the radially expandable flexible members 20 so that the fluid flows through the isolated spaces 28. The fluid flows out of the distal end 31 to the anatomical region of interest. As such, the physician is able to employ the insertion tube 14 along with the sheath 12 to irrigate the anatomical region of interest. Prior to, during or after irrigating the anatomical region of interest, suction can be applied through the outflow channels 32 to remove fluid and/or debris from the anatomical region of interest.

Figure 3A:
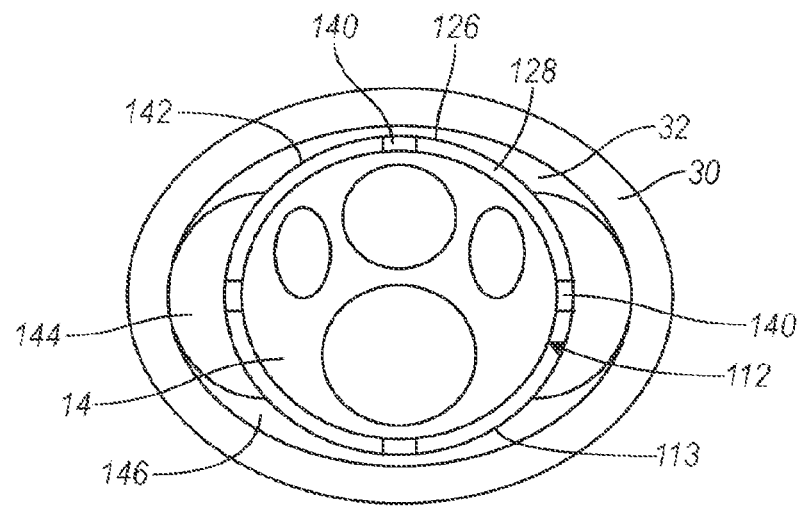
FIGS. 3A and 3B are end views of another sheath for an endoscope in accordance with the principles of the present invention.
Figure 3B:
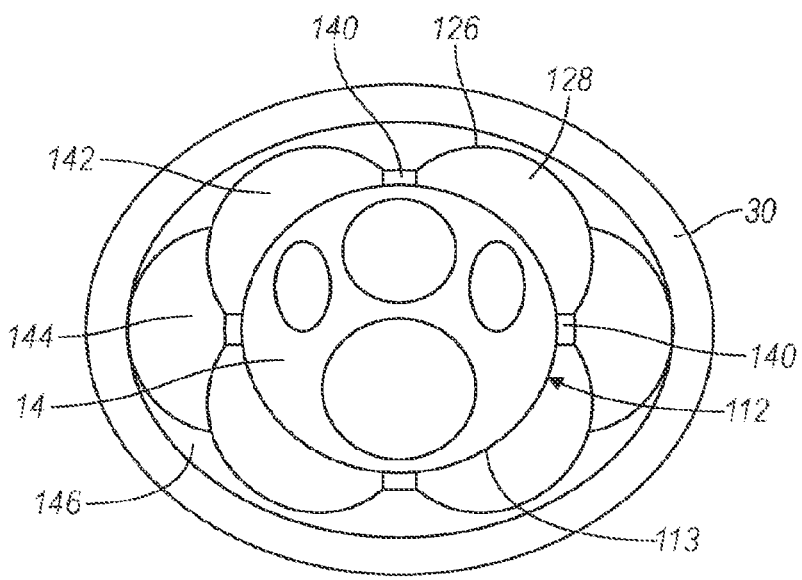

Turning now to FIGS. 3A and 3B, there is shown another sheath 112 in accordance with the principles of the present invention. The sheath 112 includes a plurality of radially expandable flexible members 126 which extend along the length of a sheath body 113. The plurality of radially expandable flexible members 126 are attached to the sheath body at a plurality of anchor points 140 along the length of the sheath body 113. The plurality of radially expandable flexible members 126 expand during active fluid inflow from the inlet 20 to the distal end of the sheath 112. The radially expandable flexible members 126 are spaced apart along the sheath body 13 to define one or more isolated spaces 128 that extend between adjacent radially expandable flexible members 126 when the radially expandable flexible members are inflated within the ureter 30. When expanded, the radially expandable flexible members 126 generally form the shape of a semi-circle.

A plurality of outflow channels 32 extend along the length of the sheath body 113. The outflow channels 32 remove debris from a body region during active fluid outflow. The sheath 112 also includes a plurality of radially expanding members 142 attached to the sheath body 113 at a plurality of anchor points 140 along the length of the sheath body 13. The radially expandable flexible members 142 are spaced apart along the sheath body 113 to define one or more isolated spaces 144 that extend between adjacent radially expandable flexible members 146 when the radially expandable flexible members 142 are inflated within the ureter 30. The plurality of radially expandable flexible members 142 expand during active fluid inflow from the proximal end of the sheath to the distal end of the sheath 12 through the inlet 20 and into a region of interest.

Figure 4:
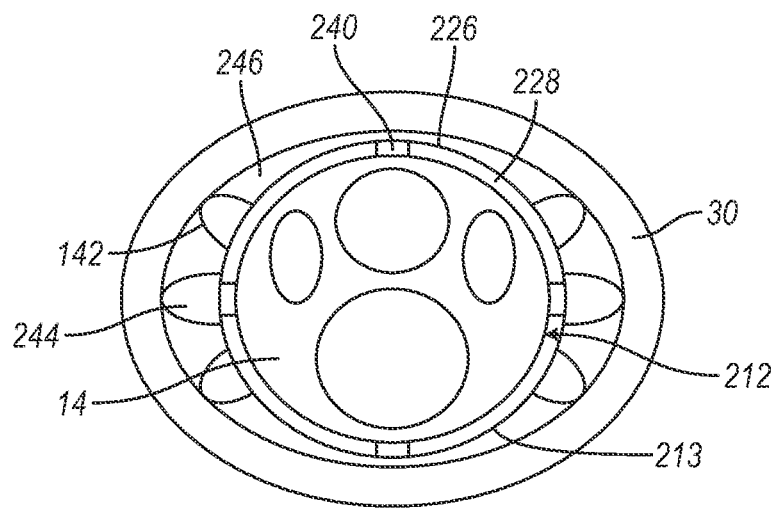
FIG. 4 is an end view of yet another sheath for an endoscope in accordance with the principles of the present invention.

Turning now to FIG. 4, there is shown yet another sheath 212 in accordance with the principles of the present invention. The sheath 212 includes a plurality of radially expandable flexible members 226 which extend along the length of a sheath body 213. The plurality of radially expandable flexible members 226 are attached to the sheath body at a plurality of anchor points 240 along the length of the sheath body 213. The plurality of radially expandable flexible members 226 expand during active fluid inflow from the inlet 20 to the distal end of the sheath 212. The radially expandable flexible members 226 are spaced apart along the sheath body 213 to define one or more isolated spaces 228 that extend between adjacent radially expandable flexible members 226 when the radially expandable flexible members are inflated within the ureter 30.

The sheath 212 also includes a plurality of ribs 142 that extend along the length of the sheath body 213. The plurality of ribs 142 may be rigid in nature such that they do not collapse when external pressure is applied. A plurality of outflow channels 246 extend along the length of the sheath body 213. And the plurality of ribs 142 define a plurality of outflow channels 244 that extends along the length of the sheath body 213. The outflow channels 244 and 246 remove debris from a body region during active fluid outflow.

Figure 5:
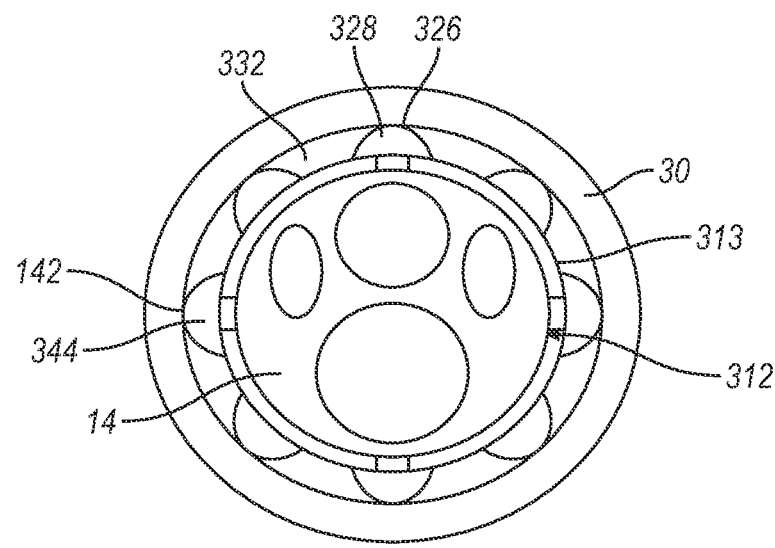
FIG. 5 is an end view of yet another sheath for an endoscope in accordance with the principles of the present invention.

FIG. 5 illustrates yet another sheath 312 in accordance with the principles of the present invention. The sheath 12 includes a plurality of radially expandable flexible members 326 which extend along the length of a sheath body 313. Each of the plurality of radially expandable flexible members 326 has a generally semicircular cross-sectional shape when expanded as shown in FIG. 5. The plurality of radially expandable flexible members 326 are attached to the sheath body 313 at a plurality of anchor points along the length of the sheath body 313. The plurality of radially expandable flexible members 326 expand during active fluid inflow from the inlet 20 to the distal end of the sheath 12 and into a region of interest. The radially expandable flexible members 326 are spaced apart along the sheath body 313 to define one or more isolated spaces 328 that extend between adjacent radially expandable flexible members 326 when the radially expandable flexible members are inflated within the ureter 30.

A plurality of outflow channels 332 and 344 extend along the length of the sheath body 313. It is contemplated that some of channels 326 may be rigid and permit fluid outflow while some of the channels may be radially expandable and allow for fluid inflow. The outflow channels 332 and 344 may remove debris from a body region during active fluid outflow.

Figure 6:
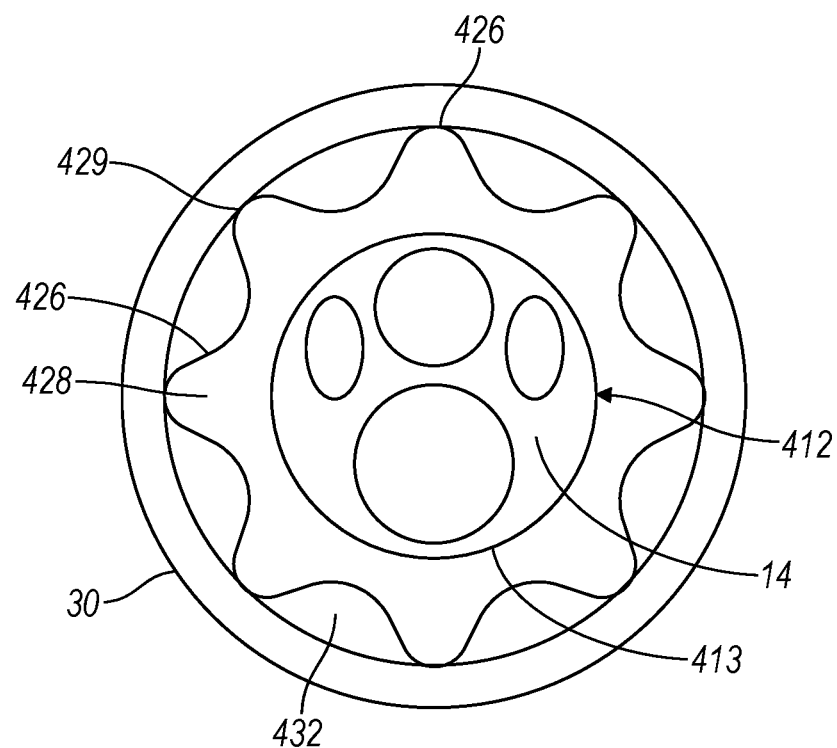
FIG. 6 is an end view of yet another sheath for an endoscope in accordance with the principles of the present invention.

Turning now to FIG. 6, there is shown a sheath 412 in accordance with the principles of the present invention. The sheath 412 includes a plurality of radially expandable flexible regions 426 which extend along a length of the sheath body 413. Each of the plurality of radially expandable flexible regions 426 has a generally rounded end 429. The plurality of radially expandable flexible regions 426 are attached to the sheath body 413 at a plurality of anchor points along the length of the sheath body 413. The plurality of radially expandable flexible regions 426 expand during active fluid inflow from the inlet 20 to the distal end of the sheath 12. The radially expandable flexible regions 426 are spaced apart along the sheath body 413 to define an isolated space 428 that extends along the sheath body 413 when the radially expandable flexible regions 426 are inflated within the ureter 30.

The radially expandable flexible regions 426 further define a plurality of outflow channels 432 that extend along the length of the sheath body 413. The outflow channels 432 remove debris from a body region during active fluid outflow.

Figure 7:
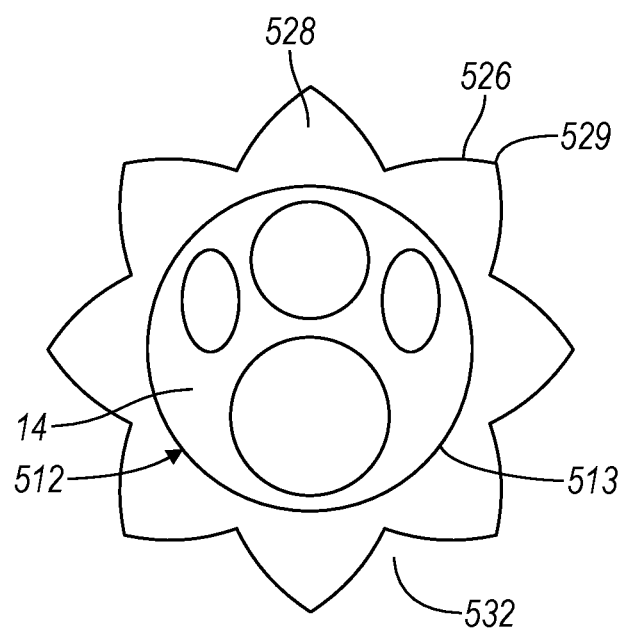
FIG. 7 is an end view of yet another sheath for an endoscope in accordance with the principles of the present invention.

Turning now to FIG. 7, there is shown a sheath 512 in accordance with the principles of the present invention. The sheath 512 includes a plurality of radially expandable flexible regions 526 which extend along the length of a sheath body 513. Each of the plurality of radially expandable flexible regions 526 has a generally pointed end 529. The plurality of radially expandable flexible members 526 are attached to the sheath body 513 at a plurality of anchor points along the length of the sheath body. The plurality of radially expandable flexible regions 526 expand during active fluid inflow from the inlet 20 to the distal end of the sheath 12. The radially expandable flexible members 526 are spaced apart along the sheath body 513 to define an isolated space 528 that extends along the sheath body 513 when the radially expandable flexible regions 526 are inflated within the ureter 30.

The radially expandable flexible regions 526 further define a plurality of outflow channels 532 that extend along the length of the sheath body 513. The outflow channels 532 remove debris from a body region during active fluid outflow.

Figure 8:
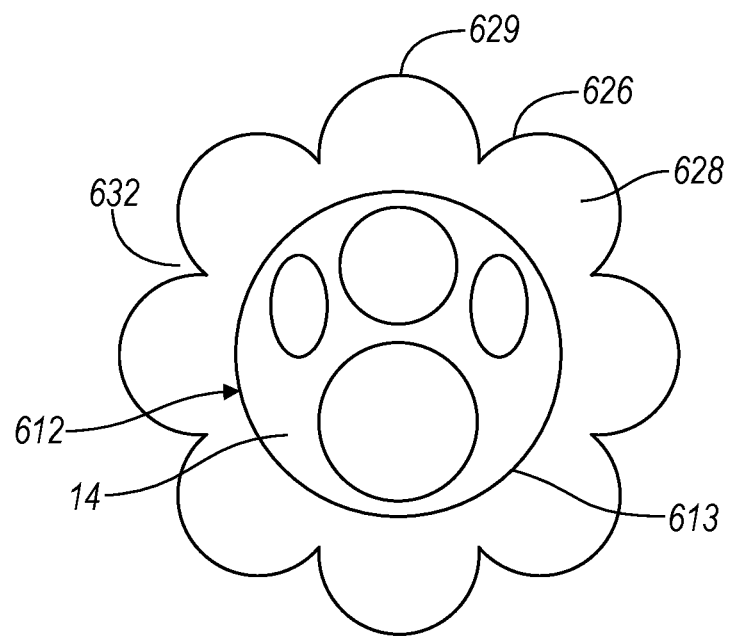
FIG. 8 is an end view of yet another sheath for an endoscope in accordance with the principles of the present invention.

Referring now to FIG. 8, there is shown a sheath 612 in accordance with the principles of the present invention. The sheath 612 includes a plurality of radially expandable flexible regions 626 which extend along the length of a sheath body 613. Each of the plurality of radially expandable flexible regions 626 has a generally semi-circular cross-sectional shape 629. The plurality of radially expandable flexible regions 626 are attached to the sheath body 613 at a plurality of anchor points along the length of the sheath body 613. The plurality of radially expandable flexible regions 626 expand during active fluid inflow from the inlet 20 to the distal end of the sheath 12. The radially expandable flexible regions 626 are spaced apart along the sheath body 613 to define an isolated space 628 that extends along the sheath body 613 when the radially expandable flexible members 626 are inflated within the ureter 30.

The radially expandable flexible regions 626 further define a plurality of outflow channels 632 that extend along the length of the sheath body 613. The outflow channels 632 remove debris from a body region during active fluid outflow.

Figure 9:
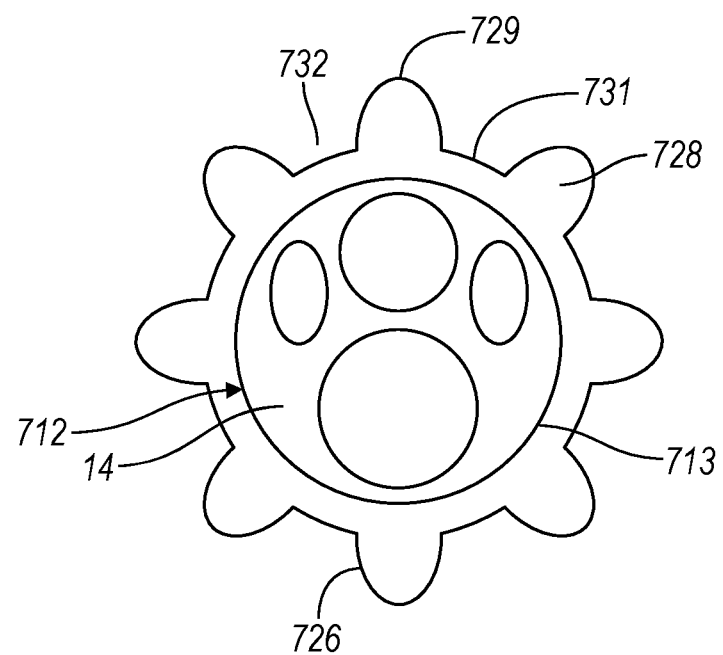
FIG. 9 is an end view of yet another sheath for an endoscope in accordance with the principles of the present invention.

Turning now to FIG. 9, there is shown a sheath 712 in accordance with the principles of the present invention. The sheath 712 includes a plurality of radially expandable flexible regions 726 which extend along the length of a sheath body 713. Each of the plurality of radially expandable flexible regions 726 has a generally elongated petal shape with a rounded end 729. The plurality of radially expandable flexible regions 726 are attached to the sheath body 713 at a plurality of anchor points along the length of the sheath body 713. The plurality of radially expandable flexible regions 726 expand during active fluid inflow from the inlet 20 to the distal end of the sheath 12. The radially expandable flexible regions 726 are spaced apart along the sheath body 713 to define an isolated space 728 that extends along the sheath body 713 when the radially expandable flexible members 726 are inflated within the ureter 30.

The radially expandable flexible members 726 further define a plurality of outflow channels 732 that extend along the length of the sheath body 713. The outflow channels 732 remove debris from a body region during active fluid outflow.

The description of the invention is merely exemplary in nature and variations that do not depart from the gist of the invention are intended to be within the scope of the invention. Such variations are not to be regarded as a departure from the spirit and scope of the invention.

What is claimed is:

1. A sheath capable of receiving an insertion tube of an endoscope, the sheath comprising:
   a sheath body;
   an inflow port at a proximal end of the sheath body;
   an outflow port at the proximal end of the sheath body;
   a region including a plurality of outflow channels which extend along a length of the sheath body to remove debris from an anatomical region of interest; and
   a plurality of radially expandable flexible members which extend along the length of the sheath body, the plurality of radially expandable flexible members being attached to an outer surface of the sheath body at a plurality of anchor points along the length of the sheath body, the plurality of radially expandable flexible members being configured to expand outwardly from the outer surface of the sheath during active fluid inflow from the inflow port to a distal end of the sheath, where fluid flows out of the distal end and into the anatomical region of interest, wherein an outflow channel of the plurality of outflow channels is on a radially expandable flexible member of the plurality of radially expandable flexible members, wherein the plurality of radially expandable flexible members are spaced apart along the sheath body to define (i) at least a portion of the outflow channels and (ii) one or more isolated spaces that extend between adjacent radially expandable flexible members when the plurality of radially expandable flexible members are inflated within a body passage and through which the fluid flows when it is supplied to the inflow port, wherein the one or more isolated spaces are separate from and at least partially surrounded by at least one of the plurality of outflow channels, wherein the plurality of outflow channels includes rigid channels that are attached to the plurality of radially expandable flexible members at a plurality of anchor points.

2. The sheath of claim 1, wherein the plurality of outflow channels includes rigid channels that are spaced apart to define additional isolated spaces that extend along the length of the sheath body.

3. The sheath of claim 1, wherein the active fluid inflow provides irrigation fluid to a body region.

4. The sheath of claim 1, further comprising one or more sensors located at the distal end of the sheath body.

5. The sheath of claim 4, wherein the one or more sensors measures at least one of pressure, temperature, and fluid flow rate.

6. The sheath of claim 1, wherein the plurality of outflow channels include a rigid rib disposed on one of the plurality of radially expandable flexible members.

7. A sheath capable of receiving an insertion tube of an endoscope, the sheath comprising:
  a sheath body;
  an inflow port at a proximal end of the sheath body;
  an outflow port at the proximal end of the sheath body;
  a region including a plurality of outflow channels which extend along a length of the sheath body to remove debris from an anatomical region of interest, wherein the plurality of outflow channels includes rigid channels that are attached to the sheath body at a plurality of anchor points; and
  a plurality of radially expandable flexible members which extend along the length of the sheath body, the plurality of radially expandable flexible members being attached to an outer surface of the sheath body at a plurality of anchor points along the length of the sheath body, the plurality of radially expandable flexible members being configured to expand outwardly from the outer surface of the sheath during active fluid inflow from the inflow port to a distal end of the sheath, where fluid flows out of the distal end and into the anatomical region of interest, wherein an outflow channel of the plurality of outflow channels is on a radially expandable flexible member of the plurality of radially expandable flexible members,
  wherein the plurality of radially expandable flexible members are spaced apart along the sheath body to define (i) at least a portion of the outflow channels and (ii) one or more isolated spaces that extend between adjacent radially expandable flexible members when the plurality of radially expandable flexible members are inflated within a body passage and through which the fluid flows when it is supplied to the inflow port, wherein the one or more isolated spaces are separate from and at least partially surrounded by at least one of the plurality of outflow channels.

8. A sheath capable of receiving an insertion tube of an endoscope, the sheath comprising:
  a sheath body;
  an inflow port at a proximal end of the sheath body;
  an outflow port at the proximal end of the sheath body;
  a region including a plurality of outflow channels which extend along a length of the sheath body to remove debris from an anatomical region of interest; and
  a plurality of radially expandable flexible members which extend along the length of the sheath body, the plurality of radially expandable flexible members being attached to an outer surface of the sheath body at a plurality of anchor points along the length of the sheath body, the plurality of radially expandable flexible members being configured to expand outwardly from the outer surface of the sheath during active fluid inflow from the inflow port to a distal end of the sheath, where fluid flows out of the distal end and into the anatomical region of interest, wherein an outflow channel of the plurality of outflow channels is on a radially expandable flexible member of the plurality of radially expandable flexible members,
  wherein the plurality of radially expandable flexible members are spaced apart along the sheath body to define (i) at least a portion of the outflow channels and (ii) one or more isolated spaces that extend between adjacent radially expandable flexible members when the plurality of radially expandable flexible members are inflated within a body passage and through which the fluid flows when it is supplied to the inflow port, wherein the one or more isolated spaces are separate from and at least partially surrounded by at least one of the plurality of outflow channels, wherein the plurality of outflow channels includes rigid channels having ribs that are spaced apart to define the one or more isolated spaces between adjacent ribs that extend along the length of the sheath body.

* * * * *

UNITED STATES PATENT AND TRADEMARK OFFICE
CERTIFICATE OF CORRECTION

| | | |
|---|---|---|
| PATENT NO. | : 11,730,345 B2 | Page 1 of 1 |
| APPLICATION NO. | : 15/738351 | |
| DATED | : August 22, 2023 | |
| INVENTOR(S) | : Lawrence J. St. George | |

It is certified that error appears in the above-identified patent and that said Letters Patent is hereby corrected as shown below:

On the Title Page

On page 2, in Column 2, Item (56) under "Other Publications", Line 15, delete "1604081.5," and insert --16704081.5,-- therefor In the Claims In Column 7, Line 22, in Claim 2, after "includes", insert --the--

Signed and Sealed this
Fourth Day of February, 2025

Coke Morgan Stewart
*Acting Director of the United States Patent and Trademark Office*